United States Patent
Coburn et al.

(10) Patent No.: US 9,428,445 B2
(45) Date of Patent: Aug. 30, 2016

(54) AMINE COMPOUNDS AND THEIR USE AS ZERO OR LOW VOC NEUTRALIZERS

(71) Applicant: ANGUS Chemical Company, Buffalo Grove, IL (US)

(72) Inventors: Charles E. Coburn, Vernon Hills, IL (US); William C. Miles, Collegeville, PA (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

(21) Appl. No.: 14/406,920

(22) PCT Filed: May 31, 2013

(86) PCT No.: PCT/US2013/043499
§ 371 (c)(1),
(2) Date: Dec. 10, 2014

(87) PCT Pub. No.: WO2014/003969
PCT Pub. Date: Jan. 3, 2014

(65) Prior Publication Data
US 2015/0166467 A1  Jun. 18, 2015

Related U.S. Application Data

(60) Provisional application No. 61/664,203, filed on Jun. 26, 2012.

(51) Int. Cl.
| | |
|---|---|
| *C11D 3/28* | (2006.01) |
| *C11D 3/32* | (2006.01) |
| *C11D 7/32* | (2006.01) |
| *C07C 229/24* | (2006.01) |
| *C07C 209/56* | (2006.01) |
| *C11D 3/30* | (2006.01) |
| *C07C 229/16* | (2006.01) |
| *C07C 229/22* | (2006.01) |
| *C11D 3/33* | (2006.01) |
| *C09D 7/12* | (2006.01) |
| *C09D 5/02* | (2006.01) |

(52) U.S. Cl.
CPC .......... *C07C 229/24* (2013.01); *C07C 209/56* (2013.01); *C07C 229/16* (2013.01); *C07C 229/22* (2013.01); *C09D 5/024* (2013.01); *C09D 7/1233* (2013.01); *C11D 3/30* (2013.01); *C11D 3/33* (2013.01); *C11D 7/3209* (2013.01); *C11D 7/3245* (2013.01)

(58) Field of Classification Search
CPC ......... C11D 3/30; C11D 3/33; C11D 7/3209; C11D 7/3245; C07C 209/56
USPC .............................. 510/488, 499, 505; 564/1
See application file for complete search history.

(56) References Cited

U.S. PATENT DOCUMENTS

| | | | |
|---|---|---|---|
| 3,929,678 A | 12/1975 | Laughlin et al. | |
| 4,259,217 A | 3/1981 | Murphy | |
| 2008/0219934 A1* | 9/2008 | Kim ....................... | A61K 8/046 424/47 |
| 2010/0275816 A1 | 11/2010 | Swedo | |
| 2010/0326320 A1 | 12/2010 | Swedo et al. | |

FOREIGN PATENT DOCUMENTS

| | | |
|---|---|---|
| JP | 2009165980 A | 7/2009 |
| WO | 2007020203 A1 | 2/2007 |
| WO | 2008081036 A1 | 7/2008 |
| WO | 2010126657 A1 | 11/2010 |
| WO | 2011044472 A1 | 4/2011 |

OTHER PUBLICATIONS

Database Registry, XP-002710083, Chemical Abstracts Service, Nov. 7, 2011. Database accession No. 1251267-80-7 abstract.
Database Registry, XP-002710082, Chemical Abstracts Service, Nov. 7, 2011, Database accession No. 1342152-59-3.
Office Action issued on Chinese Application 201380033805X, mailed Nov. 3, 2015 English translation only.
Communication on EP Application 13727791.9, mailed Nov. 13, 2014.
International Preliminary Report on Patentability on PCT/US2013/043499, issued Dec. 31, 2014.
International Search Report on PCT/US2013/043499, mailed Aug. 19, 2013.

* cited by examiner

*Primary Examiner* — Gregory R Delcotto
(74) *Attorney, Agent, or Firm* — Foley & Lardner LLP

(57) ABSTRACT

Provided are compounds for use as neutralizing agents in aqueous formulations. The compounds are of the formula I: (Formula I should be inserted here.) wherein R, $R^1$, $R^2$, $R^3$, $R^4$, and $R^5$ are as defined herein.

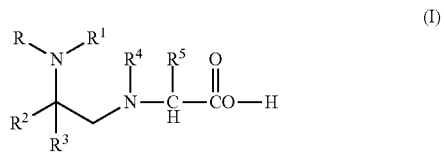

9 Claims, No Drawings

AMINE COMPOUNDS AND THEIR USE AS ZERO OR LOW VOC NEUTRALIZERS

CROSS REFERENCE TO RELATED APPLICATIONS

This application is a 35 USC §371 national phase filing of PCT/US2013/043499 filed May 31, 2013, which claims priority from provisional application Ser. No. 61/664,203, filed Jun. 26, 2012, which is incorporated herein by reference in its entirety.

BACKGROUND

This invention relates generally to amine compounds and their use as zero or low volatile organic content (VOC) neutralizer additives for various applications, such as cleaning products and paints and coatings.

Organic amines are used in many applications as neutralizing agents. In a number of geographies, manufacturers are facing regulations to reduce the volatile organic content (VOC) of their formulations. Most conventional neutralizing amines are 100% volatile and are therefore VOC contributors.

Ammonia and inorganic hydroxides and carbonates are potential alternatives for use as neutralizers, that are by definition non-VOC contributors. However, ammonia, while an efficient neutralizer, has a very strong odor and is therefore unsuitable for use in low odor paint. Inorganic hydroxides and carbonates are undesirable in some applications such as paints and coatings because they often result in coatings with poor scrub resistance.

The problem addressed by this invention is the provision of new low or no VOC neutralizing agents.

STATEMENT OF INVENTION

We have now discovered new compounds that may function as efficient neutralizers for aqueous formulations. Advantageously the compounds exhibit either low or no VOC and in some embodiments, may exhibit very low amine odor.

In one aspect, there is provided a compound of formula I:

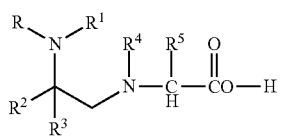

(I)

or a salt or zwitterion thereof,
wherein R, $R^1$, and $R^4$ are independently H or linear or branched $C_1$-$C_3$ alkyl;
$R^2$ and $R^3$ are independently linear or branched $C_1$-$C_6$ alkyl, or $R^2$, $R^3$, together with the carbon to which they are attached, form $C_3$-$C_8$ cycloalkyl; and
$R^5$ is H or linear or branched $C_1$-$C_6$ alkyl optionally substituted with: OH, C(=O)OH, C(=O)$NH_2$, SH, $CH_3$S, HOOCCH($NH_2$)$CH_2$S—S—$CH_2$—, phenyl, hydroxyphenyl, imidazolyl, or indoyl; or
$R^4$ and $R^5$, together with the atoms to which they are attached, form a pyrrolidine ring optionally substituted with OH.

In another aspect, there is provided a method for neutralizing an aqueous formulation identified as in need of neutralization, the method comprising using, as a neutralizing agent in the formulation, a compound of formula I as described herein.

In a further aspect, there is provided an aqueous based paint or coating comprising a neutralizing agent, a binder, a carrier, and optionally a pigment, wherein the neutralizing agent is a compound of formula I as described herein.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

"Alkyl," as used in this specification, whether alone or as part of another group (e.g., in dialkylamino), encompasses straight and branched chain aliphatic groups having the indicated number of carbon atoms. Preferred alkyl groups include, without limitation, methyl, ethyl, propyl, isopropyl, butyl, isobutyl, sec-butyl, tert-butyl, pentyl, and hexyl.

The term "cycloalkyl" refers to saturated and partially unsaturated cyclic hydrocarbon groups having the indicated number of ring carbon atoms. Preferred cycloalkyl groups include, without limitation, cyclopropyl, cyclobutyl, cyclopentyl, cyclohexyl, cycloheptyl, and cyclooctyl. The cycloalkyl is optionally substituted with linear or branched $C_1$-$C_6$ alkyl.

As noted above, in one aspect the invention provides compounds that are useful as neutralizing agents in aqueous formulations. Neutralizing agents may be included in various formulations to, for example, neutralize residual acid moieties or to raise the pH to a desired value, sometimes between about 8 and 10. Most conventional neutralizing agents currently used in many industries, including paints and coatings and cleaners, are VOC contributors. In addition, when used in an otherwise low VOC formulation, the odor of conventional neutralizing agents is more noticeable.

In contrast, the compounds of the invention are zero or very low VOC materials that may also exhibit low odor. In addition, the compounds may impart comparable performance properties to those provided by conventional neutralizing compounds. Consequently, the advantage of low VOC may be achieved with the compounds of the invention, without significant negative impact on other attributes of aqueous formulations in which they are used.

The compounds of the invention may be represented by the formula I:

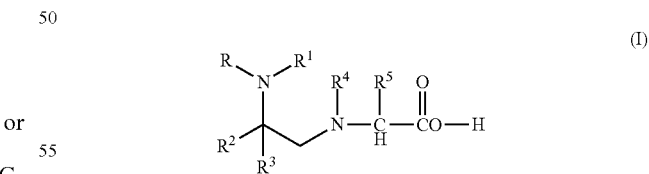

(I)

or a salt or zwitterion thereof,
wherein R, $R^1$, and $R^4$ are independently H or linear or branched $C_1$-$C_3$ alkyl;
$R^2$ and $R^3$ are independently linear or branched $C_1$-$C_6$ alkyl, or $R^2$, $R^3$, together with the carbon to which they are attached, form $C_3$-$C_8$ cycloalkyl; and
$R^5$ is H or linear or branched $C_1$-$C_6$ alkyl optionally substituted with: OH, C(=O)OH, C(=O)$NH_2$, SH, $CH_3$S, HOOCCH($NH_2$)$CH_2$S—S—$CH_2$—, phenyl, hydroxyphenyl, imidazolyl, or indoyl; or R[4] and R[5], together with the atoms to which they are attached, form a pyrrolidine ring optionally substituted with OH.

In some embodiments, the compounds of formula I are of the formula I-1, which are compounds of formula I wherein R and R[1] are both H.

In some embodiments, the compounds of formula I and I-1 are of the formula I-2, which are compounds of formula I or I-1 wherein R[2] and R[3] are independently linear or branched C1-C4 alkyl, alternatively linear or branched C1-C3 alkyl. In some embodiments, R[2] and R[3] are both methyl.

In some embodiments, the compounds of formula I, I-1, and I-2 are of the formula I-3, which are compounds of formula I, I-1, or I-2 wherein R[4] is H.

In some embodiments, the compounds of formula I, I-1, and I-2 are of the formula I-4, which are compounds of formula I, I-1, and I-2 wherein R[4] is methyl, ethyl, or propyl.

In some embodiments, the compounds of formula I, I-1, I-2, I-3, and I-4 are of the formula I-5, which are compounds of formula I, I-1, I-2, I-3, or I-4 wherein R[5] is H.

In some embodiments, the compounds of formula I, I-1, I-2, I-3, and I-4 are of the formula I-6, which are compounds of formula I, I-1, I-2, I-3, or I-4 wherein R[5] is unsubstituted linear or branched $C_1$-$C_6$ alkyl, alternatively unsubstituted linear or branched $C_1$-$C_4$ alkyl.

In some embodiments, the compounds of formula I, I-1, I-2, I-3, and I-4 are of the formula I-7, which are compounds of formula I, I-1, I-2, I-3, or I-4 wherein R[5] is linear or branched $C_1$-$C_6$ alkyl substituted with: OH, C(=O)OH, C(=O)NH$_2$, SH, CH$_3$S, HOOCCH(NH$_2$)CH$_2$S—S—CH$_2$—, phenyl, hydroxyphenyl, imidazolyl, or indoyl. In some embodiments, R[5] is linear or branched $C_1$-$C_6$ alkyl substituted with OH or C(=O)OH.

In some embodiments, the compounds of formula I, I-1, and I-2 are of the formula I-8, which are compounds of formula I, I-1, or I-2 wherein R[4] and R[5], together with the atoms to which they are attached, form a pyrrolidine ring optionally substituted with OH.

In some embodiments, the compounds of formula I, I-1, I-2, I-3, I-4, I-5, I-6, I-7, and I-9 are of the formula I-9, which are compounds of formula I, I-1, I-2, I-3, I-4, I-5, I-6, I-7, or I-9 in zwitterionic form.

In some embodiments, the compounds of formula I are as shown in Table 1 (or a salt or zwitterion thereof).

| Name | Structure |
|---|---|
| N-[2-(amino)-2-methylpropyl]-glycine | |
| 2-((2-amino-2-methylpropyl)amino)propanoic acid | |
| 2-((2-amino-2-methylpropyl)amino)-3-methylbutanoic acid | |
| 2-((2-amino-2-methylpropyl)amino)-4-methylpentanoic acid | 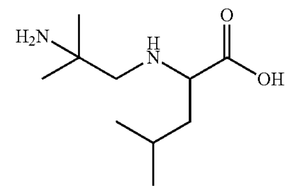 |
| 2-((2-amino-2-methylpropyl)amino)-3-hydroxypropanoic acid | 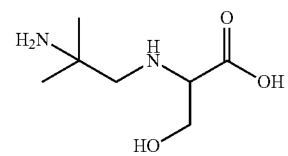 |
| 2-((2-amino-2-methylpropyl)amino)-3-hydroxybutanoic acid | 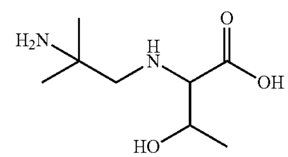 |
| 2-((2-amino-2-methylpropyl)amino)succinic acid | 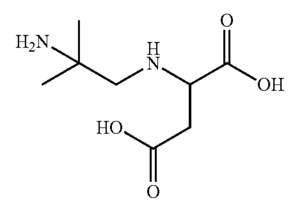 |
| 2-((2-amino-2-methylpropyl)amino) pentanedioic acid | 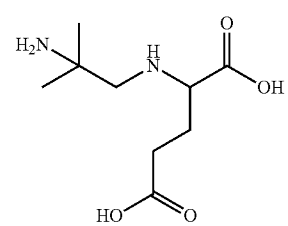 |

A preferred compound of formula I is N-[2-(amino)-2-methylpropyl]-glycine.

In some embodiments, N-[2-(dimethylamino)-2-methylpropyl]-glycine is excluded as a compound of the invention.

Compounds of formula I may be in form of salts. The counterion for the salt may be a monovalent or polyvalent cation. Examples include, without limitation, sodium ion, potassium ion, magnesium ion, or calcium ion (e.g., two compounds of formula I may use Ca$^{2+}$ as the counterion). Sodium ion is preferred.

Moreover, the acid group in the compounds of formula I may form a zwitterion by interacting with a basic nitrogen present in the molecule. In some embodiments, a zwitterion is the preferred form of the compound of formula I.

The compounds of formula I may be readily prepared. An example of a typical procedure is shown in Scheme I.

SCHEME 1

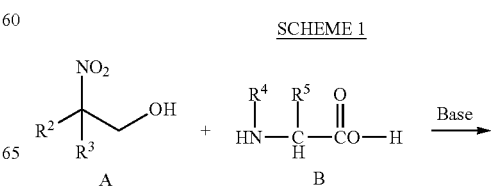

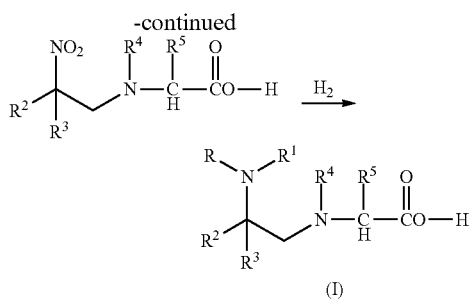

As shown in Scheme 1, compounds of the invention may be prepared by reacting a compound of formula A with a compound of formula B. When R, $R^1$ and/or $R^4$ are alkyl, an amine alkylating step (not shown) may be carried out according to techniques well known to those skilled in the art. Preferred compounds of formula A include 2-nitro-2-methyl-1-propanol. Formula A compounds are commercially available and/or may be readily synthesized by those skilled in the art.

The formula B compound is typically an amino acid or an amino acid derivative. Examples include, without limitation, glycine, alanine, valine, leucine, isoleucine, serine, threonine, cysteine, cystine, methionine, lysine, arginine, phenylalanine, tyrosine, proline, hydroxyproline, histidine, tryptophan, aspartic acid, glutamic acid, asparagine, and glutamine. Preferred amino acids include glycine, aspartic acid, glutamic acid, serine, and threonine. Particularly preferred is glycine. Formula B compounds are commercially available and/or may be readily synthesized by those skilled in the art.

The reaction may be conducted according to the above Scheme (and the Examples) using techniques well known to those skilled in the art.

The product mixture may be used as is, particularly if the reaction was run neat, or may be further purified by known methods.

The compounds of the invention are useful as neutralizing agents in aqueous formulations. The compounds exhibit low or no VOC and as a result, formulations that are overall low or no VOC may be prepared. In some embodiments, the compounds of the invention or the formulations in which they are included exhibit a vapor pressure for the organic (non-aqueous) components at 20° C. of less than 0.2 mm Hg, alternatively less than 0.1 mm Hg. In some embodiments, all organic (non-aqueous) components in a formulation of the invention, including the compounds of formula I, exhibit a boiling point of above 180° C., alternatively above 200° C., or alternatively above 216° C.

Examples of formulations in which the compounds of formula I may be included as neutralizers include, without limitation, cleaning products (household or industrial), and paint and coatings.

In a preferred embodiment, the aqueous formulation is a paint or coating. The paint or coating is used to provide a protective and/or decorative barrier for residential and industrial surfaces, such as for floors, automobiles, exteriors and interiors of houses, and other buildings. The paint or coating formulation, in addition to comprising a neutralizing agent, may also comprise a binder, a carrier, and optionally a pigment.

Pigments may be included to provide hiding power and the desired color to the final coated material and may also be used to provide bulk to the paint or coating. While multiple pigments may be present in end-use paints or coatings, sometimes only white pigment, such as titanium oxide, perhaps in combination with extender pigments such as calcium carbonate and/or kaolin clay, is added in the early stages of the formation of the formulation. Any other desired pigments of various colors (including more white pigment) can optionally be added at the later stages of, or after, the formulation is completed.

Pigments may be organic or inorganic. Examples of pigments can include, but are not limited to, titanium dioxide, kaolin clay, calcined kaolin clay, carbon black, iron oxide black, iron oxide yellow, iron oxide red, iron oxide brown, organic red pigments, including quinacridone red and metallized and non-metallized azo reds (e.g., lithols, lithol rubine, toluidine red, naphthol red), phthalocyanine blue, phthalocyanine green, mono- or di-arylide yellow, benzimidazolone yellow, heterocyclic yellow, quinacridone magenta, quinacridone violet, and the like, and any combination thereof.

Binders are included in paint and coating formulations to provide a network in which the pigment particles are dispersed and suspended. Binders bind the pigment particles together and provide integrity and adhesion for the paint or coating film. Generally, for aqueous based paints and coatings, the binders are latex based materials.

Latex binders are typically prepared by free radical initiated aqueous emulsion polymerization of a monomer mixture containing alkyl acrylate (methyl acrylate, ethyl acrylate, butyl acrylate and/or 2-ethylhexylacrylate), alkyl methacrylate, vinyl alcohol/acetate, styrene, and/or acrylonitrile and ethylene type monomers. Suitable binders include acrylic, vinyl acrylic, styrenated-acrylic, vinyl acetate ethylene based materials, or blends of these materials. The amount of the binder in the formulations of the invention can be the amount conventionally used in paint and coating formulations, which can vary widely due to the desired gloss/sheen range, and also the solids concentration, of a specific paint formulation. By way of non-limiting example, the amount of binder solids can be from about 5% to about 30% of the total formula volume.

A paint and coating formulation also contains a carrier in which the formulation ingredients are dissolved, dispersed, and/or suspended. In the aqueous based formulations contemplated by the invention, the carrier is usually water, although other water-based solutions such as water-alcohol mixtures and the like may be used. The aqueous carrier generally makes up the balance of the formulation, after all the other ingredients have been accounted for.

Other additives may be included in the paint and coating formulations besides the neutralizing agents, pigments, binders, and carriers discussed above. These include, but are not limited to, leveling agents and surfactants, thickeners, rheology modifiers, co-solvents such as glycols, including propylene glycol or ethylene glycol, corrosion inhibitors, defoamers, co-dispersants, additional aminoalcohol compounds, and biocides.

The paint and coating formulations may be manufactured by conventional paint manufacturing techniques, which are well known to those skilled in the art. Typically, the formulations are manufactured by a two-step process. First, a dispersion phase, commonly referred to as the grind phase, is prepared by mixing the dry pigments with other grind phase components, including most other solid powder formulation materials, under constant high shear agitation to provide a high viscosity and high solids mixture. This part of the process is designed to effectively wet and disagglomerate the dry pigments and stabilize them in an aqueous dispersion.

The second step of the paint manufacturing process is commonly referred to as the letdown or thindown phase, because the viscous grind is diluted with the remaining formulation components, which are generally less viscous than the grind mix. Typically, the binders, any predispersed pigments, and any other paint materials that only require mixing and perhaps moderate shear, are incorporated during the letdown phase. The letdown phase may be done either by sequentially adding the letdown components into a vessel containing the grind mix, or by adding the grind mix into a vessel containing a premix of the latex resins and other letdown components, followed by sequential addition of the final letdown components. In either case, constant agitation is needed, although application of high shear is not required.

Cleaning formulations according to the invention may comprise a neutralizing agent, a surfactant, water, and an optional solvent, wherein the neutralizing agent is a compound of formula I. The surfactant may be selected from one or more of nonionic, anionic, cationic, ampholytic, amphoteric and zwitterionic surfactants. A typical listing of anionic, ampholytic, and zwitterionic classes, and species of these surfactants, is given in U.S. Pat. No. 3,929,678. A list of suitable cationic surfactants is given in U.S. Pat. No. 4,259,217. Each of these documents is incorporated herein by reference. The surfactants may typically be present at a level of from 0.1 to 15, alternatively from 0.1 to 10, or alternatively from 0.1 to 5.0 percent by weight, based on the total weight of the formulation.

Water is generally the dominant component of the aqueous cleaning formulation and may typically comprises at least 50, more typically at least 80 and even more typically at least 90, weight percent based on the total weight of the formulation. The water is typically present at a level of less than 99.5%, more typically less than 99% and even more typically less than 98%. Deionized water is preferred. If the cleaning composition is concentrated, then the water may be present in the composition at a concentration of less than 85 wt. %.

Optional solvents for use in the cleaning formulation may include, for instance, any water miscible solvent, such as ethylene oxide based or propylene oxide based glycol ethers, sugar alcohols, polyols, fatty acid methyl esters, etc. Solvents that are low VOC and in particular exhibit a vapor pressure of lower than 0.1 mm Hg at 20° C. are preferred and may include, for instance, glycol ether solvents such as propyleneglycol n-butyl ether, propyleneglycol n-propyl ether, dipropylenenglycol methyl ether, dipropylenegylycol propyl ether, dipropylenegylycol n-butyl ether, tripropyleneglycol n-butyl, and tripropyleneglycol methyl ether. When used, the optional solvent may typically be present in the formulation in an amount ranging from 0.1 to 10 weight percent, alternatively 0.1 to 5.0 weight percent, or alternatively from 0.5 to 2.0 weight percent, based on the total weight of the formulation.

Other additives known for use in cleaning formulations may be included such as, without limitation, alkaline agents, builders, fragrances, preservatives, biocides, colorants, dyes and rheology modifiers. These optional additives are used in known quantities and in known ways.

The compounds of formula I of the invention are typically added to an aqueous formulation at one or more steps during the formulation manufacturing process. For instance, when the formulation is a paint or coating, the compound may be added at one or more of three different places: to the pigment dispersion, to the binder dispersion, and/or in a final addition to the paint formulation.

The amount of compound of formula I used may typically be determined based on the desired pH of the formulation. Typically, an amount of the compound is added so as to provide a final pH in the range of about 7 to 11, alternatively about 8 to 10, or alternatively about 8.5 to 9.5. In some embodiments, inorganic bases, such as sodium hydroxide, may also be used, together with the compounds of formula I, to further facilitate the neutralization properties.

In a further aspect, the invention provides a method for reducing the volatile organic compound content of an aqueous formulation that contains a neutralizing agent. The method comprises using as the neutralizing agent an effective amount of a compound of formula I. As noted above, an effective amount is typically the quantity required to provide a pH of about 7 to 11, alternatively about 8 to 10, or alternatively about 8.5 to 9.5, in the formulation.

As noted above, the compounds of the invention function as zero or low VOC and low odor neutralizers for aqueous formulations. Some embodiments of the invention will now be described in detail in the following Examples.

EXAMPLES

Example 1

N-[2-(amino)-2-methylpropyl]-glycine (Sodium Salt)

Preparation of the Glycine-Mono-NMP Molecule:

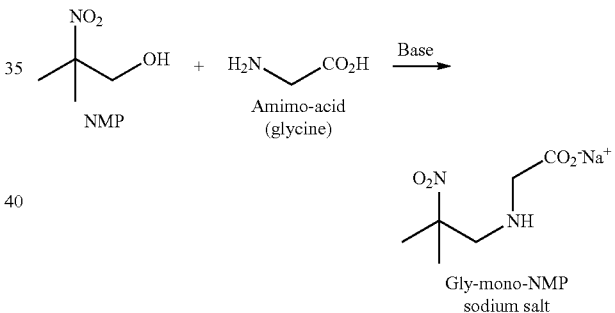

Into a weighed 1 liter round-bottomed flask equipped with a magnetic stirrer is added glycine (37.5 g, 0.50 mols). To this is added methanol (MeOH, 50 g) and the flask is stirred to afford a white slurry. A 50 wt % caustic solution (42.0 g, 0.525 mols, 1.05 equivalences) is added all at once and the flask sealed under nitrogen with stirring. A slight exotherm is detected and after 30 mins the contents of the flask become a clear, colorless, homogeneous solution. The resulting sodium glycinate solution is concentrated in vacuo using a rotary evaporator. The temperature and vacuum are both slowly increased (80° C./0.5 torr) over time. After 3 hrs at 80° C., the flask is removed and re-weighed to ensure that all of the water has successfully been removed (49.5 g, 99.6% yield).

Methanol (100 g) is added into the flask and the contents are magnetically stirred (30 min at 40° C.) until a fine, white slurry results. To this is added a methanolic solution of 2-nitro-2-methyl-propanol (NMP, 59.5 g, 0.50 mols, 50 g methanol) and the reaction is run at 40° C. After 2 hrs, the reaction mixture becomes translucent. The heating is turned off for the day and the reaction is allowed to stir overnight.

MeOH (100 g) is added to the flask and the solids are broken-up and the reaction continued (35° C.) for an additional 3.5 hr. The resulting reaction mixture is placed into the refrigerator (5° C.) over the week-end. The solid is isolated and rinsed with cold ether (10 g), filtered, and dried under reduced pressure. The solid is characterized by $^1$H-NMR (CD$_3$OD, ppm) 1.6 (s), 3.0 (s), 3.1 (s), 4.9 (s); $^{13}$C-NMR (CD$_3$OD, ppm) 34, 65, 69, 100, 189; FTIR (KBr, cm$^{-1}$) 3335 (s), 2990 (m), 1620 (m), 1430 (m), 1350 (m), 1120 (m); and LC/MS (m/z) calculated 199.0695. found 199.0622. All spectra are consistent with the structure assigned.

Preparation of the Glycine-Mono-AMP Molecule:

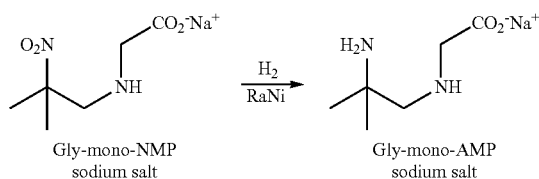

Gly-mono-NMP sodium salt → Gly-mono-AMP sodium salt

A 2 liter stainless steel (SS) autoclave is charged with 3111 Raney Nickel (RaNi) catalyst (9.9 g wet weight, about 4.5 g dry weight, 4.6 wt %) and MeOH (450 g) before being connected to a Parr apparatus, purged with nitrogen, and pressurized with hydrogen (650 psig). The autoclave is stirred, warmed to 40° C., and the addition of the crude reaction mixture of the Glycine-Mono-NMP (99 g, 0.50 mols) in MeOH (250 g) begun (2 ml/min). The autoclave is heated to 75° C. and the addition continued for 2 hours. Once the addition of the crude Glycine-Mono-NMP is complete the lines are flushed with MeOH (25 ml) and the reaction is held at 75° C. for an additional 30 mins before being cooled to 45° C. The autoclave is vented, and the contents are vacuum filtered to remove the RaNi catalyst. The clear, light purple filtrate (925 g) is transferred into a 3 liter pear shaped flask, and concentrated in vacuo (ultimately 80° C./0.5 torr) to remove residual solvents. This affords the Glycine-Mono-AMP (77.6 g, 84% yield) as a grey bubbled solid. This solid is dissolved into deionized water (100 g) and washed with ether (3×25 ml) to remove organic soluble impurities. The resulting brown aqueous solution is concentrated in vacuo (80° C./0.5 torr) to afford a grey solid (77.4 g). This solid is dissolved into warm absolute ethanol (EtOH, 150 g) and vacuum filtered. The filtrate is concentrated in vacuo (80° C./0.50 torr) to afford the purified Glycine-Mono-AMP adduct (68.1 g, 81% yield) as grey solid that is sealed under nitrogen. The sample shows the following: $^1$H-NMR (CD$_3$OD, ppm) 1.1 (s, 6H), 2.5 (s, 2H), 3.2 (s, 2H); $^{13}$C-NMR (CD$_3$OD, ppm) 38.1, 60.7, 65.4, 73.2, 189.4; FTIR (KBr, cm$^{-1}$) 3335 (m), 2960 (m), 1590 (s), 1415 (m), 1300 (m), 1130 (m); LC/MS (m/z) calculated 169.0953. found 169.0903. All spectra were consistent with the structure assigned.

Example 2

VOC Characteristics

Zero VOC can be defined in one of three ways according to California Air Resources Board (CARB) Method 310 for VOC determination: the vapor pressure can be below 0.1 mm Hg at 20° C., the boiling point can be above 216° C., or the compound must pass a gas chromatograph test (EPA Method 18, 8240B, 8260B, ASTM D859-000, or NIOSH Method 1400).

Thermal analysis (TGA) shows that there is no boiling point for the N-[2-(amino)-2-methylpropyl]-glycine (sodium salt) of Example 1 and that the material decomposes above a temperature of 275° C. The material also has no discernable vapor pressure and does not elute on the GC because it cannot be vaporized and so will pass the GC testing methods for CARB compliance. Thus, this material can be classified as a zero VOC using any of the three methods outlined in CARB Method 310.

The acid dissociation constants (pK$_a$) for the Example 1 compound are measured to be 9.9 and 6.1 using a standard titration method for the primary amine and the sodium carboxylate, respectively. Also using titration, the neutral equivalent is determined to be 168, which matches the molecule's molecular weight. However, upon inclusion into a paint formulation, slightly less (2%) of this molecule is needed to regulate pH than a control compound (2-amino-2-ethyl-1,3-propanediol (AEPD)) with a measured neutralization equivalent of 124. Thus, the second pK$_a$ contributes to pH regulation and contributes to the value of the compound as a neutralizer in paint formulations.

Example 3

2-((2-Amino-2-methylpropyl)amino)propanoic Acid (prophetic)

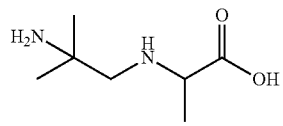

The title compound may be prepared through substantially the same procedure as described in Example 1, using alanine as the starting amino acid.

Example 4

2-((2-Amino-2-methylpropyl)amino)-3-methylbutanoic acid

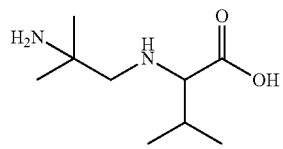

The title compound may be prepared through substantially the same procedure as described in Example 1, using valine as the starting amino acid.

Example 5

2-((2-Amino-2-methylpropyl)amino)-4-methylpentanoic acid

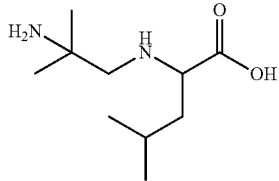

The title compound may be prepared through substantially the same procedure as described in Example 1, using leucine as the starting amino acid.

Example 6

2-((2-Amino-2-methylpropyl)amino)-3-hydroxypropanoic acid

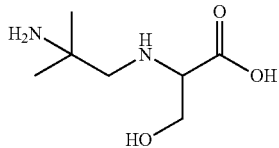

The title compound may be prepared through substantially the same procedure as described in Example 1, using serine as the starting amino acid.

Example 7

2-((2-Amino-2-methylpropyl)amino)-3-hydroxybutanoic acid

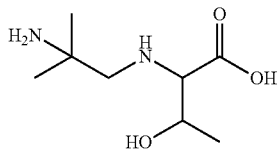

The title compound may be prepared through substantially the same procedure as described in Example 1, using threonine as the starting amino acid.

Example 8

2-((2-Amino-2-methylpropyl)amino)succinic acid

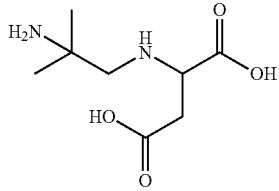

The title compound may be prepared through substantially the same procedure as described in Example 1, using aspartic acid as the starting amino acid. As would be recognized by one skilled in the art, an additional equivalent of base should be used for the synthesis.

Example 9

2-((2-Amino-2-methylpropyl)amino)pentanedioic acid

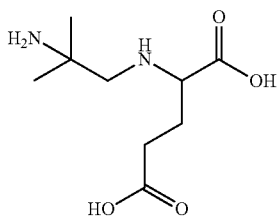

The title compound may be prepared through substantially the same procedure as described in Example 1, using glutamic acid as the starting amino acid. As would be recognized by one skilled in the art, an additional equivalent of base should be used for the synthesis.

We claim:

1. A compound of formula I:

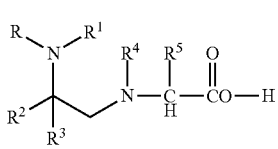

or a salt or zwitterion thereof,
wherein R and $R^1$ are each H;
$R^4$ is H or linear or branched $C_1$-$C_3$ alkyl;
$R^2$ and $R^3$ are independently linear or branched $C_1$-$C_6$ alkyl, or $R^2$, $R^3$, together with the carbon to which they are attached, form $C_3$-$C_8$ cycloalkyl; and
$R^5$ is H or linear or branched $C_1$-$C_6$ alkyl optionally substituted with: OH, C(=O)OH, C(=O)$NH_2$, SH, $CH_3$S, HOOCCH($NH_2$)$CH_2$S—S—$CH_2$—, phenyl, hydroxyphenyl, imidazolyl, or indoyl; or
$R^4$ and $R^5$, together with the atoms to which they are attached, form a pyrrolidine ring optionally substituted with OH.

2. The compound of claim 1 wherein $R^5$ is H.

3. The compound of claim 1 wherein $R^5$ is unsubstituted linear or branched $C_1$-$C_6$ alkyl.

4. The compound of claim 1 wherein $R^5$ is linear or branched $C_1$-$C_6$ alkyl substituted with OH or C(=O)OH.

5. The compound of claim 1 that is: N-[2-(amino)-2-methylpropyl]-glycine; 2-((2-amino-2-methylpropyl)amino)propanoic acid; 2-((2-amino-2-methylpropyl)amino)-3-methylbutanoic acid; 2-((2-amino-2-methylpropyl)amino)-4-methylpentanoic acid; 2-((2-amino-2-methylpropyl)amino)-3-hydroxypropanoic acid; 2-((2-amino-2-methylpropyl)amino)-3-hydroxybutanoic acid; 2-((2-amino-2-methylpropyl)amino)succinic acid; or 2-((2-amino-2-methylpropyl)amino)pentanedioic acid.

6. A method for neutralizing an aqueous formulation identified as in need of neutralization, the method comprising using, as a neutralizing agent in the formulation, the compound of claim 1.

7. The method of claim 6 wherein the formulation is an aqueous based paint or coating, or a cleaning product.

8. An aqueous based paint or coating comprising a neutralizing agent, a binder, a carrier, and an optional pigment, wherein the neutralizing agent is a compound of claim 1.

9. A cleaning formulation comprising a neutralizing agent, a surfactant, and water, wherein the neutralizing agent is a compound of claim 1.

* * * * *